US012734127B1

(12) United States Patent
Ling et al.

(10) Patent No.: US 12,734,127 B1
(45) Date of Patent: Sep. 15, 2026

(54) TRANSMUCOSAL FILM FOR TREATING INSOMNIA

(71) Applicant: Xiamen LP Pharmaceutical Co., Ltd., Xiamen (CN)

(72) Inventors: Rongbin Ling, Xiamen (CN); Liyuan Chen, Xiamen (CN); Zhoue Gao, Xiamen (CN); Avinash Singh, Xiamen (CN); Haijian Zhu, Xiamen (CN)

(73) Assignee: XIAMEN LP PHARMACEUTICAL CO., LTD., Xiamen (CN)

( * ) Notice: Subject to any disclaimer, the term of this patent is extended or adjusted under 35 U.S.C. 154(b) by 0 days.

(21) Appl. No.: 19/429,766

(22) Filed: Dec. 22, 2025

(30) Foreign Application Priority Data

Dec. 9, 2025 (CN) ......................... 202511845097.0

(51) Int. Cl.

| | |
|---|---|
| ***A61K 9/00*** | (2006.01) |
| ***A61K 31/191*** | (2006.01) |
| ***A61K 31/197*** | (2006.01) |
| ***A61K 31/4045*** | (2006.01) |
| ***A61K 31/4415*** | (2006.01) |
| ***A61K 47/02*** | (2006.01) |
| ***A61K 47/10*** | (2017.01) |
| ***A61K 47/20*** | (2006.01) |
| ***A61K 47/26*** | (2006.01) |
| ***A61K 47/32*** | (2006.01) |
| ***A61K 47/36*** | (2006.01) |
| ***A61K 47/38*** | (2006.01) |
| ***A61K 47/40*** | (2006.01) |
| ***A61P 25/20*** | (2006.01) |

(52) U.S. Cl.
CPC ............ *A61K 9/006* (2013.01); *A61K 9/0056* (2013.01); *A61K 31/191* (2013.01); *A61K 31/197* (2013.01); *A61K 31/4045* (2013.01); *A61K 31/4415* (2013.01); *A61K 47/02* (2013.01); *A61K 47/10* (2013.01); *A61K 47/20* (2013.01); *A61K 47/26* (2013.01); *A61K 47/32* (2013.01); *A61K 47/36* (2013.01); *A61K 47/38* (2013.01); *A61K 47/40* (2013.01); *A61P 25/20* (2018.01)

(58) Field of Classification Search
None
See application file for complete search history.

(56) References Cited

U.S. PATENT DOCUMENTS

2020/0383962 A1* 12/2020 Bernardo ............. A61K 9/7007

FOREIGN PATENT DOCUMENTS

EP 4431091 A1 * 9/2024 ........... A61K 36/185

* cited by examiner

*Primary Examiner* — Sin J Lee
(74) *Attorney, Agent, or Firm* — Ashurst Perkins Coie US LLP; Viola T. Kung

(57) ABSTRACT

The present invention provides an oral transmucosal film for delivering four active ingredients of melatonin, GABA (gamma-aminobutyric acid), vitamin B5, and vitamin B6 through the sublingual mucosa. The film is a tri-layer structure containing amorphous active ingredients, one or more solubilizers, one or more antioxidants, one or more form stabilizers, and one or more hydrophobic stabilizers to deliver the drug through a transmucosal route. Comparing with an oral tablet, the present oral transmucosal film provides better treatment for insomnia. The oral sublingual film is a tri-layer film; the upper layer comprises melatonin, the middle layer comprises GABA and vitamin B6, and the lower layer comprises vitamin B5. The combination of the four active ingredients in a tri-layer oral transmucosal film provides a better treatment for insomnia than other existing methods.

15 Claims, No Drawings

TRANSMUCOSAL FILM FOR TREATING INSOMNIA

This application claims the priority of Chinese Application No. 202511845097.0, filed Dec. 9, 2025, which is incorporated herein by reference in its entirety.

FIELD OF INVENTION

The present invention provides a tri-layer sublingual film for delivering active ingredients of melatonin, gamma-aminobutyric acid, vitamin B6, and vitamin B5 through the sublingual mucosa. The sublingual film is a stable film and is effective for treating insomnia.

BACKGROUND OF THE INVENTION

Insomnia is a common sleep disorder that can make it hard to fall asleep or stay asleep, or both. It also can cause individuals to wake up too early and not be able to get back to sleep. Insomnia can drain a patient's energy level and affect mood. It also can affect health, work performance, and quality of life. Short-term insomnia lasts for days or weeks and is usually due to stress or a distressing event. But some people have long-term insomnia, also called chronic insomnia. This lasts for three months or more. Insomnia may be the main problem, or it may be related to other medical conditions or medicines.

Melatonin is an essential component in the regulation of circadian rhythm in humans, specifically the sleep cycle. Several studies initially demonstrated that melatonin has a sleep-regulating effect due to its production during the night; it is therefore widely used as a supplement for the treatment of sleep disorders such as insomnia, anxiety, and jet lag.

Research by Grima et al. (BMC Medicine (2018) 16:8, DOI 10.1186/s12916-017-0995-1) mentions that melatonin supplementation significantly reduced global Pittsburgh Sleep Quality Index scores relative to placebo, indicating melatonin improved sleep quality, increased sleep efficiency on actigraphy, and improved vitality and mental health on the SF-36 v1 questionnaire ($p \leq 0.05$ for each). Also, melatonin decreased anxiety on the Hospital Anxiety Depression Scale and fatigue on the Fatigue Severity Scale ($p \leq 0.05$ for both).

The bioavailability of melatonin tablets is approximately 15%; this indicates that melatonin undergoes extensive first pass metabolism, which results in longer Tmax and lower Cmax. Samira et al. (Drugs in R&D (2023) 23:257-265) report that sublingual submission of melatonin spray resulted in an early and high plasma melatonin peak (Cmax: 2332±950 μg/mL; Tmax: 23.3±6.5 min) compared to tablet intake (Cmax: 1151±565 μg/mL; Tmax: 64.2±44.2 min).

Adequate vitamin B5 levels contribute to the production of serotonin, a precursor to melatonin. By supporting a healthy serotonin-melatonin conversion process, vitamin B5 promotes relaxation and helps people fall asleep more quickly and easily, reducing the time spent tossing and turning in bed. Vitamin B5 and sleep are intricately linked. Vitamin B5 affects sleep quality through its role in producing vital neurotransmitters such as acetylcholine, serotonin, and melatonin. Vitamin B5's positive impacts on adrenal gland function help regulate cortisol production, thus improving the body's stress response and promoting better sleep. Vitamin B5 is needed to make coenzyme A, the cofactor required to make cortisol in the adrenal glands and acetylcholine in the brain. Acetylcholine is a key neurotransmitter in sleep.

Gamma-aminobutyric acid (GABA) is the main inhibitory neurotransmitter in the central nervous system. Studies have shown its ability to improve insomnia. GABA functions in a dynamic equilibrium with Glutamate, which has an excitatory effect on neurons, but in excess produces neurotoxicity, leading to neuronal death and neurological disorders. GABA is produced by the enzyme glutamic acid decarboxylase (GAD), which catalyzes the decarboxylation of Glutamate, and the production of GABA produces an inhibitory effect on the excitatory properties of Glutamate in order to maintain the neural excitability/inhibition balance. The study by Li et al. (Biomedicine & Pharmacotherapy, 103, 509-516, 2018) shows that insomniac mice had up-regulated GABA expression in vivo through treatment, with a decrease in Glutamate content and an increase in the GABA/Glutamate ratio, resulting in sedative and hypnotic functions and improved insomnia.

Several studies of oral natural or biosynthetic GABA administration to insomniacs have reported improvements in sleep onset and maintenance, morning drowsiness, recovery of fatigue scores, and facilitation of the natural induction of sleep, but a minimum of 1 week of GABA use is required to achieve the effect.

A lack of vitamin B6 has been linked to symptoms of insomnia and depression. Vitamin B6 aids in the production of the hormones serotonin and melatonin, both of which are important to sound, restful sleep and also to mood. Vitamin B6 is also an essential nutrient for synthesizing GABA. Vitamin B6, mainly including pyridoxine, pyridoxal, and pyridoxamine, is a water-soluble vitamin. The pilot study of Lemoine (Complementary Therapies in Medicine 45:104-108, 2019) suggests that the combination of melatonin, vitamin B6, and medicinal plants may be beneficial in mild-to-moderate insomnia.

Melatonin, a white-cream to yellowish crystalline powder that is also known as N-acetyl-5-methoxytryptamine, is a type of indoleamine derived primarily from the essential amino acid tryptophan (TRP). Melatonin is soluble in ethanol and slightly soluble in water; it has the following structure:

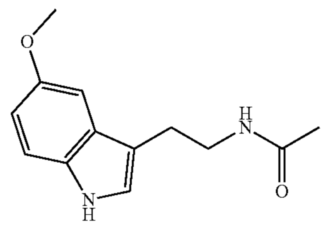 [SMILES: COc1ccc2[nH]cc(CCNC(C)=O)c2c1]

Gamma-aminobutyric acid (GABA), a white crystalline powder that is also known as 4-aminobutanoic acid, is a neurotransmitter, a chemical messenger in the brain. GABA is freely soluble in water; it has the following structure:

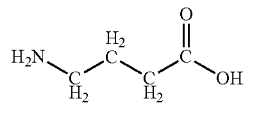

Vitamin B5 is also known as pantothenic acid. In the present invention, vitamin B5 or its salt form such as calcium pantothenate or sodium pantothenate can be used.

Salt of pantothenic acid is a white to off-white powder and freely soluble in water. Vitamin B5 has the following structure:

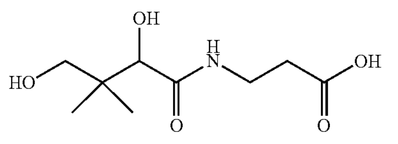

Vitamin B6 is composed of three compounds: pyridoxine, pyridoxal, and pyridoxamine. Pyridoxine contains a methylhydroxyl group (—$CH_3OH$), pyridoxal contains an aldehyde group (—CHO), and pyridoxamine contains an aminomethyl group (—$CH_3NH_2$). After administration, all three can be metabolically converted to the active forms, pyridoxal phosphate and pyridoxamine phosphate. Pyridoxine is a white solid powder, soluble in water, and has the following structure:

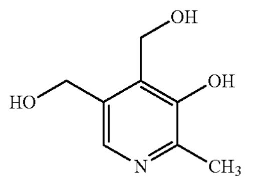

Insomnia has now become a major health problem of global concern, with about one-third of the population suffering from sleep problems, a proportion that is still rising year by year. Di et al (JAMA Network Open. 2022; 5 (11): e2240788. doi: 10.1001/jamanetworkopen.2022.40788) report that a high percentage of U.S. adults experience long-term sleep deprivation, chronic social jet lag, and frequent sleep disturbances. De et al report that the prevalence of trouble sleeping was 29.8% and the prevalence of daytime sleepiness was 27.2%.

Most patients with insomnia use drug therapy, with benzodiazepines, such as diazepam, eszopiclone, and alprazolam, being the most commonly used medications. However, the unclear pathogenesis of insomnia complicates the development of hypnotic drugs that effectively target its underlying mechanisms. Consequently, these medications often lead to various side effects, such as addiction, withdrawal symptoms, and daytime fatigue, which can significantly harm both physical and mental health. Therefore, finding a safer and more effective treatment for insomnia has become urgent.

DETAILED DESCRIPTION OF THE INVENTION

The present invention provides a pharmaceutical composition suitable for sublingual administration of active ingredients to treat insomnia. The pharmaceutical composition is an oral transmucosal film comprising active ingredients of melatonin, GABA, vitamin B5, and vitamin B6; the film provides fast absorption and quick onset of action. The oral transmucosal film of the present invention is placed below the tongue to disintegrate or dissolve by the saliva within a few minutes. The active ingredients are absorbed directly into the blood vessels via sublingual mucosa, which avoids gastrointestinal degradation and bypasses the liver first pass effect, and consequently the absorption rate is improved dramatically compared with oral tablets, granules, or solutions. Transmucosal films are convenient to carry and use and are suitable for patients who have difficulty swallowing, and thus they improve patient compliance.

The inventors have discovered that the combination of melatonin with other active ingredients GABA, vitamin B5, and vitamin B6 is more effective than melatonin alone in treating insomnia. The present invention provides improved and stable therapeutic dosage for the treatment of insomnia by combining melatonin, GABA, vitamin B5, and vitamin B6. Vitamin B6 aids in the production of melatonin and reduces insomnia linked with vitamin B6 deficiency. GABA is a key inhibitory neurotransmitter that slows down the brain activity, making it easier for a subject to fall asleep and also significantly reducing the time needed to fall asleep. Vitamin B5 plays a vital role in synthesizing essential neurotransmitters, including acetylcholine, serotonin, and melatonin. These neurotransmitters are vital for regulating sleep-wake cycles and promoting restful sleep, making vitamin B5 a true sleep aid.

The present invention is directed to an oral sublingual tri-layer film useful for treating insomnia. The tri-layer film comprises: (a) an upper layer comprising 5-50% by weight melatonin, 40-80% by weight of a first film-forming material, 0.5-5% by weight of a first solubilizer, 8-20% by weight of a first amorphous form stabilizer, and 0.5-10% by weight of a first hydrophobic stabilizer; (b) a middle layer comprising 16.7-38.9% by weight of gamma-aminobutyric acid (GABA), 3-20% by weight of vitamin B6, 38-53% by weight of a second film-forming material, 1.5-6% by weight of an antioxidant, 0.5-5% by weight of a second solubilizer, and 8-20% by weight of a second amorphous form stabilizer; and (c) a lower layer comprising 16.65-50% by weight of vitamin B5, 40-72% by weight of a third film-forming material, 8-20% by weight of a third amorphous form stabilizer, and 2-8% by weight of a second hydrophobic stabilizer.

In the present film, the film-forming material is selected from the group consisting of: hypromellose (HPMC), hydroxypropyl cellulose (HPC), polyethylene glycol and polyvinyl alcohol graft copolymer (PEG-PVA), polyvinyl alcohol (PVA), polyvinyl pyrrolidone (PVP), hydroxyethyl cellulose, pullulan, sodium carboxymethyl cellulose (CMC-Na), xanthan gum, tragacanth gum, guar gum, polyacrylic acid, high amylose starch, hydroxypropylated high amylose starch, collagen, gelatin pectin, copovidone, povidone, and any combination thereof. Preferred film-forming materials are HPMC, HPC, PVA, pectin, PVP, gelatin, hydroxyethyl cellulose, and pullulan.

In the present film, the solubilizer is selected from the group consisting of: hydroxypropyl-β-cyclodextrins, sodium lauryl sulfate, polysorbate, poloxamers, and any combination thereof.

In the present film, the hydrophobic stabilizer is selected from the group consisting of: talc, stearic acid, magnesium stearate, calcium stearate, sodium stearyl fumarate, and any combination thereof.

In the present film, the antioxidant is selected from the group consisting of: butylated hydroxytoluene, butylated hydroxyanisole, citric acid, ascorbyl palmitate, gallic acid monohydrate, and any combination thereof.

In the present film, the amorphous form stabilizer is selected from the group consisting of sodium alginate, polyvinyl pyrrolidone, chitosan, polyethylene glycol, and any combination thereof.

The present oral transmucosal film combines melatonin, GABA, vitamin B5, and vitamin B6 in specific doses for an effective treatment of insomnia. The present oral transmucosal film mitigates the instability issues of the active ingredients and provides a robust and stable film. To resolve the stability issue, tri-layer films are provided in which each layer contains different active ingredient(s). Melatonin is in the upper layer for a fast release and an initial onset effect. GABA is in the middle layer because GABA is very hygroscopic and it melts if exposed to the environment, so GABA is designed to be sandwiched between the upper layer and the lower layer. Vitamin B6 is compatible with GABA, so vitamin B6 is included in the middle layer with GABA. Vitamin B5 and GABA are incompatible with each other, so they will undergo degradation if present in the same layer. Therefore, vitamin B5 is in the lower layer to be separated from GABA. Vitamin B5 is stable at neutral pH, and is not stable in acidic or basis condition. During the preparation of the lower layer suspension, the pH of the suspension is neutral to keep vitamin B5 stable.

The sublingual epithelium is a relatively permeable non-keratinized tissue, where blood vessels drain directly into the jugular vein. The oral transmucosal film of the present invention promotes the absorption of drugs immediately and reduces Tmax compared to oral tablets. The present sublingual film is designed to achieve faster release and action. The oral transmucosal film of the present invention is suitable for transmucosal delivery of melatonin, GABA, vitamin B5, and vitamin B6 with fast and prolonged action.

The transmucosal film provided by the invention has drug uniformity, good dissolution rate, good absorption rate, and acceptable taste. The dissolution of drugs is improved by selecting excipients and using a proper solvent or a solvent mixture for each layer during manufacturing. The transmucosal film of the present invention has a good stability and palatability. The drugs in film are absorbed through the sublingual mucosa into blood, which reduces the time to reach a peak plasma concentration (Tmax), compared to oral tablets. Drugs in the present invention enter the bloodstream through absorption, so the administration is not affected by food.

"About," when used in this application, refers to ±10%, preferably ±5%, of the recited value.

Unless otherwise specified, % used in this application refers to weight by weight %.

The active ingredient "vitamin B5," as used in this invention, refers to pantothenic acid or pantothenate, including the free base or a pharmaceutically acceptable salt thereof, such as sodium or calcium salt.

The amount of vitamin B5 in the film is about 1-10 mg, preferably 2-10 mg or 2-6 mg.

The amount of melatonin in the film is about 0.50-15 mg, preferably 0.55-12 mg or 0.55-10 mg.

The amount of GABA in the film is about 1-15 mg, preferably 2-10 mg or 3-7 mg.

The amount of vitamin B6 in the film is about 0.25-5 mg, preferably 0.5-5 mg or 0.5-2 mg.

In the present film, the active ingredients in all three layers are in an amorphous state.

The inventors have discovered that when using an amorphous form of a drug to prepare a transmucosal film, the drug is rapidly dissolved and absorbed at a fast absorption rate.

The amount of the film-forming materials in the upper layer is about 25-85% w/w, 30-85% w/w, 35-85% w/w, 35-80% w/w, 40-85% w/w, or 40-80% w/w. The amount of the film-forming materials in the middle layer is about 20-65% w/w, 25-60% w/w, 30-65% w/w, 35-60% w/w, 35-55% w/w, or 38-53% w/w. The amount of the film-forming materials in the lower layer is about 25-85% w/w, 25-80% w/w, 35-85% w/w, 40-85% w/w, or 40-72% w/w. The film-forming materials have good compatibility with all the drugs in the three layers and they provide good drug loading capacity.

The present tri-layer film selectively includes suitable excipients such as amorphous form stabilizers, solubilizers, and hydrophobic stabilizers, to contribute to faster dissolution and stable dosage form.

The amorphous form stabilizers added in the film retain the amorphous forms of active ingredients in the three layers throughout the shelf life of the film. The amorphous form stabilizers are generally polymers, which create gel-like structures and hinder the conversion of the active ingredients from an amorphous form to a crystalline form. The amorphous form stabilizers in the film include, but are not limited to, one or more of polyvinyl pyrrolidone (PVP), hypromellose (HPMC), polyvinyl alcohol (PVA), sodium alginate, sodium carboxymethyl cellulose (CMC-Na), chitosan, polyacrylic acid, polyethylene glycol, and copovidone. Preferred amorphous form stabilizers are sodium alginate, polyvinyl pyrrolidone, chitosan, polyethylene glycol, and any combination thereof. The upper layer in general comprises about 5-30% by weight of an amorphous form stabilizer, preferably 8-20%. The middle layer in general comprises about 5-25% by weight of an amorphous form stabilizer, preferably 8-20%. The lower layer in general comprises about 5-25% by weight of an amorphous form stabilizer, preferably 8-20%.

One or more hydrophobic stabilizers are used in the upper layer and in the lower layer to protect the permeation of moisture and to improve the stability of the film. In the present tri-layer film, GABA is in the middle layer and is hygroscopic. In the present film, hydrophobic stabilizers are added in the upper layer and the lower layer to protect GABA from moisture. As GABA is already sandwiched between the two layers, it is not necessary to add a hydrophobic stabilizer in the middle layer.

The hydrophobic stabilizer protects the film from moisture absorption. Pharmaceutically acceptable hydrophobic stabilizers include magnesium aluminum silicate, talc, stearic acid, glyceryl behenate, calcium stearate, stearic acid, hydrogenated vegetable oil, magnesium stearate, and sodium stearyl fumarate. Preferred hydrophobic stabilizers are talc, stearic acid, magnesium stearate, calcium stearate, and sodium stearyl fumarate. The amount of the hydrophobic material in the upper layer is about 0.5-15% w/w, preferably 0.5-10% w/w. The amount of hydrophobic material in the lower layer is about 1-15% w/w, preferably 2-8% w/w.

The present oral transmucosal film includes one or more solubilizers to improve the dissolution and penetration of the drugs through buccal mucosa. The solubilizers include sodium lauryl sulfate (SLS), hydroxypropyl-β-cyclodextrins, polyvinyl caprolactam-polyvinyl acetate-polyethylene glycol graft copolymer, polysorbate such, dioctyl sodium sulfosuccinate, and poloxamers. Preferred solubilizers are hydroxypropyl-β-cyclodextrins, sodium lauryl sulfate, polysorbate, and poloxamers. The upper layer in general comprises about 0.5-8% by weight of a solubilizer, preferably 0.5-5%. The middle layer in general comprises about 0.5-8% by weight of a solubilizer, preferably 0.5-5%.

To mask the bitter taste of the drugs and to increase patient compliance, one or more flavoring agents and optionally one or more sweeteners are added to the one or more layers of the tri-layer film of the present invention. The active ingredient (the drug), or a pharmaceutically acceptable salt, is blended with the flavoring and sweetening agent in the presence of one or more film-forming materials to mask the bitter taste, thus improving the compliance of a patient.

Examples of flavoring agents include menthol, peppermint oil, orange flavor, pineapple flavor, cherry flavor, apple flavor, banana flavor, blueberry flavor, peach flavor, mango flavor, and grape flavor. Preferred flavors are menthol and peppermint oil.

Examples of sweeteners include sucralose, sucrose, glucose, sodium saccharin, fructose, xylitol, stevia, aspartame, neotame, acesulfame potassium, starch syrup, maltitol, erythritol, sorbitol, mannitol, and trehalose. Sucralose, acesulfame potassium, and aspartame are preferred sweeteners. The amounts of a flavor in each layer, such as the upper layer and the middle layer, are independently about 0.5-10% w/w, preferably about 0.5-5% w/w.

In one embodiment, the film further contains one or more plasticizers in the lower layer to improve the folding endurance of film and manufacturing processability. A suitable plasticizer includes polyethylene glycol (PEG), glycerin, sorbitol, propylene glycol, polysorbate, or triethyl citrate. The amount of plasticizer is 0.5-8% by weight, preferably 0.5-5% by weight.

Optionally, the film further contains one or more pigments to improve the aesthetic appearance, such as titanium dioxide or those pigments contained in FD&C or D&C.

In one embodiment, the present sublingual film containing melatonin, GABA, vitamin B5, and vitamin B6 is manufactured in the form of a tri-layer film. The upper layer comprises melatonin 5-50% by weight, 40-80% by weight of a film-forming material, 0.5-5% by weight of a solubilizer, 0.5-5% by weight of a flavoring agent, 8-20% by weight of a form stabilizer, and 0.5-10% by weight of a hydrophobic stabilizer; the middle layer comprises GABA (gamma-aminobutyric acid) 16.70-38.89% by weight, vitamin B6 3-20% by weight, 38-53% by weight of a film-forming material, 1.5-6% by weight of an antioxidant, 0.5-5% by weight of a solubilizer, 0.5-5% by weight of a flavoring agent, and 8-20% by weight of a form stabilizer; and the lower layer comprises vitamin B5 16.65-50% by weight, 40-72% by weight of a film-forming material, 8-20% by weight of a form stabilizer, 2-8% by weight of a hydrophobic stabilizer, and 0.5-5% by weight of a plasticizer. All the drugs are present in an amorphous state in the film.

The drugs from the sublingual film are rapidly absorbed through the oral mucosa and enter the bloodstream. This application was demonstrated in a study carried out using a protocol of randomized double-blind, placebo-controlled parallel design performed on 26 middle-aged patients (40-55 years) with primary insomnia.

The present invention provides a method for preparing a tri-layer sublingual film. The instability of GABA and vitamin B5 makes the process of preparing tri-layer film difficult. If GABA is not sandwiched between the layers and covered by hydrophobic stabilizer, the high hygroscopicity of the drug will cause it to absorb moisture, form an oily appearance, and undergo an oxidation reaction. For vitamin B5, if the microenvironment of neutral pH is not maintained, it will undergo degradation and interact with other drugs. For all the APIs (active pharmaceutical ingredients), if a suitable amorphous form stabilizer in the required quantity is not added, the API will undergo a form conversion from amorphous to crystalline, which leads to a non-uniform appearance of the film and extends the dissolution time of the film.

The present invention provides a method for preparing a tri-layer sublingual film that resolves the issues described above.

The method comprises the following steps:

(a) Preparing the upper layer:
- Dissolve melatonin and optionally a flavoring agent in a solvent.
- Add a first solubilizer and optionally one or more sweeteners and one or more coloring agents, and stir until a clear solution forms.
- Add a first film-forming material and stir until a clear viscous solution forms.
- Add a first hydrophobic agent and stir until uniform suspension forms.

(b) Preparing the middle layer:
- Dissolve GABA, vitamin B6, and optionally a flavoring agent in a solvent.
- Add a second solubilizer, an antioxidant, and optionally one or more sweeteners and one or more coloring agents, and stir until a clear solution forms.
- Add a second amorphous form stabilizer and a second film-forming agent and stir until a clear, viscous solution forms.

(c) Preparing the lower layer:
- Dissolve vitamin B5 in a solvent, then optionally add a color agent, and stir until a clear solution forms.
- Add a third film-forming agent and stir until a clear viscous solution forms.
- Add a second hydrophobic stabilizer and optionally a plasticizer, and stir until uniform suspension forms.

(d) Coating on substrate:
- First coat the lower layer suspension on a substrate, and dry the lower layer suspension.
- Coat the middle layer suspension on the dried lower layer and dry the middle layer suspension.
- Coat the upper layer suspension on the dried middle layer suspension.
- Remove the dried three-layer film from the substrate to form the oral transmucosal film.

Melatonin is slightly soluble in water and freely soluble in certain organic solvents. GABA, vitamin B6, and vitamin B5 are soluble in water. During manufacturing, each active ingredient is dissolved in a proper solvent, and recrystallization of each active ingredient is avoided during the process. The present manufacturing process preferably uses one solvent mixture to solubilize all the drugs completely and to keep an amorphous form of the drugs in the film. The amorphous form of drugs in the sublingual film provides good solubility, thus improving the absorption rate of drugs into the blood. A preferred solvent mixture is alcohol and water with a volume ratio of about 2:3 to 4:1; a preferred ratio is 1:1 to 2:1. For example, a preferred solvent mixture is 40-80% alcohol in water, or 50% alcohol in water. A preferred alcohol is ethanol.

The drying temperature in all the layers of manufacturing is about 30°-100° C., preferably about 40°-90° C.

In the present process, all the drugs are in an amorphous form in the film, which produces a faster dissolution rate and improves the absorption rate of all four drugs.

The substrate on which the film is formed includes, but is not limited to, polyethylene terephthalate, polypropylene resins, and polymethylpentene resins.

After step (d), the film is optionally cut into a suitable size and shape, and then further wrapped or packaged.

The sublingual film of the present invention has a length of about 1-4 cm and a width of about 1-4 cm; preferably, the film has a length of about 1-3 cm and a width of about 1-3 cm.

The present invention also provides a method for administering the present sublingual film to a subject. The method comprises identifying a subject in need thereof, and placing the film under the tongue or sublingual mucosa of the subject. The method is suitable to insomnia.

The present film is useful in treating a subject that is a mammal. The present invention is particularly useful in treating mammals including humans.

The following examples further illustrate the present invention. These examples are intended merely to be illustrative of the present invention and are not to be construed as being limiting.

EXAMPLES

Example 1: Single-Layer Film: Melatonin

In this example, melatonin sublingual films were prepared according to the formulation and process below.

| Formula: | |
|---|---|
| Melatonin | 3.00 (16.67% w/w) |
| Hydroxypropyl Cellulose SSL | 14.635 (81.31% w/w) |
| Sodium Lauryl Sulfate | 0.03 (0.17% w/w) |
| Sucralose | 0.3 (0.67% w/w) |
| FDC Red | 0.035 (0.19% w/w) |
| 60% Ethanol | 32.5 |
| Total | 18 |

Manufacturing Process:

Dissolve melatonin in solvent, then add sodium lauryl sulfate and sucralose, and stir until a clear solution forms.

Add hydroxypropyl cellulose to the above solution and continue stirring for 25 minutes or until a uniform clear viscous solution forms.

Finally add FDC Red and stir for another 15 minutes.

Coat the defoamed viscous solution in uniform thickness on a substrate at a coating temperature of about 70° C. to 90° C. to form a film on the conveyor belt.

After the film is formed, cut the film into a suitable size, and shape and pack it in a pouch or in a suitable container.

Melatonin film prepared according to the above formula and process had good film property and was easy to remove from the substrate. In the dissolution test, the drug release was fast and complete.

TABLE 1

| Dissolution Test Result of Example 1 | | | | | | |
|---|---|---|---|---|---|---|
| Media | pH 6.8 phosphate buffer, Volume 500 ml, USP II paddle method, rotation speed 50 rpm | | | | | |
| Time (min) | 5 | 10 | 15 | 20 | 30 | 45 |
| Dissolved (%) | 50 | 72 | 89 | 95 | 99 | 99 |

Example 2: Single-Layer Film: Melatonin+GABA+Vitamin B5+Vitamin B6

In this example, melatonin was combined with vitamin B5, vitamin B6, and gamma-aminobutyric acid (GABA), and sublingual films were prepared in amorphous form, with 50% ethanol used as solvents.

| Formula: | |
|---|---|
| Melatonin | 3.00 (13.64% w/w) |
| GABA (gamma-aminobutyric acid) | 3.00 (13.64% w/w) |
| Vitamin B6 | 1.00 (4.55% w/w) |
| Vitamin B5 | 2.00 (9.09% w/w) |
| HPMC 615 | 11.88 (54.00% w/w) |
| Sucralose | 0.44 (2.00% w/w) |
| menthol | 0.33 (1.50% w/w) |
| sodium lauryl sulfate | 0.33 (1.50% w/w) |
| FDC Red | 0.02 (0.09% w/w) |
| 50% Ethanol | 80 |
| Total | 22.00 |

Manufacturing Process:

Dissolve menthol and then vitamin B5 in solvent, and then dissolve melatonin, GABA, and Vitamin B6 one after another, stirring continuously.

Dissolve sodium lauryl sulfate and sucralose, and stir until a clear solution forms.

Add hydroxypropyl cellulose to the above solution and continue stirring for 40 minutes or until a uniform clear viscous solution forms.

Finally add FDC Red and stir for another 15 minutes.

Coat the defoamed viscous solution in uniform thickness on a substrate at a coating temperature of about 70° C. to 90° C. to form a film on the conveyor belt.

After the film is formed, cut the film into a suitable size, and shape and pack it in a pouch or in a suitable container.

Sublingual film prepared according to the above formula and process had good film property, smooth appearance, uniform color, and was easy to remove from the substrate.

TABLE 2

| Dissolution Test Result of Example 2 | | | | | | |
|---|---|---|---|---|---|---|
| | Media | pH 6.8 phosphate buffer, Volume 500 ml, USP II paddle method, rotation speed 50 rpm | | | | |
| | Time (min) | 5 | 10 | 15 | 20 | 30 |
| Melatonin | Dissolved | 35 | 50 | 88 | 95 | 99 |
| GABA | (%) | 66 | 89 | 96 | 98 | 98 |
| Vitamin B5 | | 41 | 60 | 83 | 96 | 100 |
| Vitamin B6 | | 65 | 90 | 97 | 100 | 100 |

In the stability study, it was found that the appearance of the Example 2 film was not good. An oily surface was seen and the amounts of GABA and vitamin B5 were reduced after 1 month. Due to the hygroscopic nature of GABA, the oily surface of the film was seen after 2 weeks of the stability study.

TABLE 3

Stability Data of Example 2 in Accelerated Condition(40° C./75% RH)

| Parameters | Description | Melatonin | GABA | Vitamin B5 | Vitamin B6 |
|---|---|---|---|---|---|
| | | Assay(%) | | | |
| Initial | Smooth and uniform red color film | 99.60 | 100.31 | 100.01 | 99.80 |
| 15 days | Red color film with slightly oily surface | 99.80 | 98.22 | 97.66 | 100.02 |
| 1 month | Change to slightly yellow and oily surface | 99.48 | 90.54 | 91.58 | 99.59 |
| 3 months | Yellow and non-uniform surface | 99.50 | 84.63 | 89.59 | 99.61 |
| 6 months | Yellow and non-uniform surface | 99.23 | 80.11 | 86.73 | 99.33 |

The stability results show that vitamin B5 and GABA undergo degradation in accelerated conditions with time. After 1 month of the stability study, the appearance of the film was not good because the amorphous form of API was converting to crystalline.

Example 3: Non-Clinical Study Comparing Single-Layer Films of Examples 1 and 2

Freshly prepared films of Examples 1 and 2 were used to study the sleep onset latency and sleep duration.

Eight participants were selected. All participants had an identifiable sleep complaint and confirmed diagnosis of chronic insomnia, and their medical histories were corroborated from hospital records.

A randomized placebo-controlled double-blind, two-treatment study was performed. Four non-pregnant woman aged 40-50 years and four men aged 40-50 years were selected. The seven-day study was performed under the supervision of a medical doctor (sleep physician) to ensure compliance of the participants.

Throughout the study, each participant completed a sleep diary retrospectively upon waking to determine time of sleep onset, time of waking, and sleep duration. The supervising doctor regularly cross-checked the diaries. The study results are shown in Table 4. Example 1 has only melatonin. Example 2 and tablets both have all four ingredients.

TABLE 4

Non-Clinical Study Results

| Parameter | Example 1 | Example 2 | Tablet with similar dosage |
|---|---|---|---|
| Sleep duration | 4.5-7 hours | 5.5-9 hours | 4.5-6 hours |
| Onset of sleep | 1-2 hours | 0.75-1.25 hours | 1.75-2.75 hours |

The study result shows that the film of Example 1 (melatonin only) improves the sleep duration but not the onset of sleep. The film of Example 2 (melatonin+GABA+vitamin B5+vitamin B6) improves both duration and onset of sleep.

Comparing Example 2 to tablets, Example 2 was found better because of faster absorption and bypassing first pass metabolism. The bioavailability of Example 2 should be better.

Example 4: Single-Layer Film: Formulation with Antioxidants and Hydrophobic Stabilizers In this example, antioxidants (BHT or ascorbic acid) and hydrophobic stabilizers (talc or stearic acid) are added to the formula of Example 2. The manufacturing process was the same as in Example 2.

Formulation:

| Example | 4-1 | 4-2 | 4-3 | 4-4 |
|---|---|---|---|---|
| Melatonin | 3.00 (13.64% w/w) | 3.00 (13.64% w/w) | 3.00 (13.64% w/w) | 3.00 (13.64% w/w) |
| GABA (gamma-aminobutyric acid) | 3.00 (13.64% w/w) | 3.00 (13.64% w/w) | 3.00 (13.64% w/w) | 3.00 (13.64% w/w) |
| Vitamin B6 | 1.00 (4.55% w/w) | 1.00 (4.55% w/w) | 1.00 (4.55% w/w) | 1.00 (4.55% w/w) |
| Vitamin B5 | 2.00 (9.09% w/w) | 2.00 (9.09% w/w) | 2.00 (9.09% w/w) | 2.00 (9.09% w/w) |
| HPMC 615 | 11.22 (51.00% w/w) | 11.22 (51.00% w/w) | 10.78 (49.00% w/w) | 10.78 (49.00% w/w) |
| BHT | 0.66 (3.00% w/w) | — | — | — |
| Ascorbic acid | — | 0.66 (3.00% w/w) | — | — |
| Talc | — | — | 1.10 (5.00% w/w) | — |
| Stearic acid | — | — | — | 1.10 (5.00% w/w) |
| Sucralose | 0.44 (2.00% w/w) | 0.44 (2.00% w/w) | 0.44 (2.00% w/w) | 0.44 (2.00% w/w) |
| menthol | 0.33 (1.50% w/w) | 0.33 (1.50% w/w) | 0.33 (1.50% w/w) | 0.33 (1.50% w/w) |
| SLS | 0.33 (1.50% w/w) | 0.33 (1.50% w/w) | 0.33 (1.50% w/w) | 0.33 (1.50% w/w) |
| FDC Red | 0.02 (0.09% w/w) | 0.02 (0.09% w/w) | 0.02 (0.09% w/w) | 0.02 (0.09% w/w) |
| 50% Ethanol | 80 | 80 | 80 | 80 |
| Total | 22.00 mg | 22.00 mg | 22.00 mg | 22.00 mg |

The stability study of Example 4 was conducted at an accelerated condition.

TABLE 5

Stability Data of Examples 4-1 and 4-2 in Accelerated Condition (40° C./75%RH)

| | Film Appearance | GABA Stability | | Vitamin B5 Stability | |
|---|---|---|---|---|---|
| Example | 4-1 and 4-2 | 4-1 | 4-2 | 4-1 | 4-2 |
| Parameters | Description | Assay (%) | | | |
| Initial | Smooth and uniform red color film | 100.11 | 99.87 | 100.23 | 99.90 |
| 15 days | Red color film with slightly oily surface | 98.73 | 98.99 | 99.68 | 99.09 |
| 1 month | Red color film with slightly oily surface | 93.58 | 92.57 | 98.63 | 97.39 |
| 3 months | Red color film with non-uniform surface | 89.33 | 86.33 | 97.57 | 95.11 |
| 6 months | Red color film with non-uniform surface | 86.57 | 83.51 | 95.43 | 90.43 |

TABLE 6

| Stability Data of Examples 4-3 and 4-4 in Accelerated Condition (40° C./75%RH) | | | | | |
|---|---|---|---|---|---|
| | Film Appearance | GABA Stability | | Vitamin B5 Stability | |
| Example Parameters | 4-3 and 4-4 Description | 4-3 | 4-4 | 4-3 | 4-4 |
| | | Assay (%) | | | |
| Initial | Smooth and uniform red color film | 100.11 | 99.87 | 100.23 | 99.90 |
| 15 days | Smooth and uniform red color film | 100.11 | 100.11 | 98.78 | 98.69 |
| 1 month | Red color film with slightly oily surface | 97.38 | 97.59 | 96.33 | 96.21 |
| 3 months | Slightly yellow and non-uniform surface | 92.23 | 93.11 | 93.67 | 94.00 |
| 6 months | Yellow and non-uniform surface | 89.59 | 89.99 | 91.53 | 91.49 |

The results show that the addition of antioxidants BHT or ascorbic acid (Examples 4-1 and 4-2) improves the stability of vitamin B5 more than GABA. The results of the film with BHT (Example 4-1) as antioxidant are better than the film with ascorbic acid (Example 4-2). There is no significant difference between Example 4-3 and Example 4-4 with different hydrophobic stabilizers. After 1 month of the stability study, the appearance of the film was not good because the amorphous form of API was converting to crystalline. Therefore, the inventors decided to add polymer to retain the amorphous nature.

Example 5: Single-Layer Film, Formulation with Different Polymers as Form Stabilizer In these experiments, PVP, PEG 8000, and Chitosan each were used as a polymer to retain the amorphous form of the active ingredients. The manufacturing process was the same as in Example 2.

| Formulation: | | | |
|---|---|---|---|
| Example | 5-1 | 5-2 | 5-3 |
| Melatonin | 3.00 (13.64% w/w) | 3.00 (13.64% w/w) | 3.00 (13.64% w/w) |
| GABA (gamma-aminobutyric acid) | 3.00 (13.64% w/w) | 3.00 (13.64% w/w) | 3.00 (13.64% w/w) |
| Vitamin B6 | 1.00 (4.55% w/w) | 1.00 (4.55% w/w) | 1.00 (4.55% w/w) |
| Vitamin B5 | 2.00 (9.09% w/w) | 2.00 (9.09% w/w) | 2.00 (9.09% w/w) |
| HPMC 615 | 9.02 (41.00% w/w) | 9.02 (41.00% w/w) | 9.02 (41.00% w/w) |
| PVP | 2.20 (10.00% w/w) | — | — |
| PEG 8000 | — | 2.20 (10.00% w/w) | — |
| Chitosan | — | — | 2.20 (10.00% w/w) |
| BHT | 0.66 (3.00% w/w) | 0.66 (3.00% w/w) | 0.66 (3.00% w/w) |
| Talc | 1.10 (5.00% w/w) | 1.10 (5.00% w/w) | 1.10 (5.00% w/w) |
| Sucralose | 0.44 (2.00% w/w) | 0.44 (2.00% w/w) | 0.44 (2.00% w/w) |
| menthol | 0.33 (1.50% w/w) | 0.33 (1.50% w/w) | 0.33 (1.50% w/w) |
| SLS | 0.33 (1.50% w/w) | 0.33 (1.50% w/w) | 0.33 (1.50% w/w) |
| FDC Red | 0.02 (0.09% w/w) | 0.02 (0.09% w/w) | 0.02 (0.09% w/w) |
| 50% Ethanol | 80 | 80 | 87 |
| Total | 22.00 mg | 22.00 mg | 22.00 mg |

The sublingual films prepared according to the above formulas had a smooth appearance. In the stability study, it was observed that the films with PVP K30 and Chitosan retained the amorphous nature of the active ingredients, but the film with PEG showed little conversion at the end of 6 months, as observed in the appearance of the film. All the examples with different polymers showed degradation in stability at an accelerated condition. GABA was found to be hygroscopic when exposed directly to the environment, leading to formation of an oil-like appearance, so it was decided to try bilayer and tri-layer technology.

Example 6: Bilayer and Tri-Layer Films

In Example 6-1, bilayer film was prepared in which the upper layer contains melatonin and the lower layer contains the remaining three active ingredients. In Example 6-2, tri-layer film was prepared in which the upper layer contains melatonin, the middle layer contains the remaining three active ingredients, and the lower layer is a protective layer without any active ingredient.

| | Formulation: | | |
|---|---|---|---|
| | Example | 6-1 | 6-2 |
| UL[1] | Melatonin | 3.00 (30.00% w/w) | 3.00 (30.00% w/w) |
| | Hydroxypropyl Cellulose SSL | 6.1 (61.00% w/w) | 6.1 (61.00% w/w) |
| | Talc | 0.5 (5.00% w/w) | 0.5 (5.00% w/w) |
| | Sucralose | 0.1 (1.00% w/w) | 0.1 (1.00% w/w) |
| | menthol | 0.1 (1.00% w/w) | 0.1 (1.00% w/w) |
| | SLS | 0.1 (1.00% w/w) | 0.1 (1.00% w/w) |
| | Titanium dioxide | 0.1 (1.00% w/w) | 0.1 (1.00% w/w) |
| | 50% ethanol | 50.00 | 50.00 |
| ML[2] | GABA (gamma-aminobutyric acid) | 3.00 (20.00% w/w) | 3.00 (20.00% w/w) |
| | Vitamin B6 | 1.00 (6.67% w/w) | 1.00 (6.67% w/w) |
| | Vitamin B5 | 2.00 (13.33% w/w) | 2.00 (13.33% w/w) |
| | HPMC 615 | 7.65 (51.00% w/w) | 7.65 (51.00% w/w) |
| | BHT | 0.45 (3.00% w/w) | 0.45 (3.00% w/w) |
| | Talc | 0.45 (3.00% w/w) | 0.45 (3.00% w/w) |
| | Sucralose | 0.15 (1.00% w/w) | 0.15 (1.00% w/w) |
| | menthol | 0.15 (1.00% w/w) | 0.15 (1.00% w/w) |
| | SLS | 0.15 (1.00% w/w) | 0.15 (1.00% w/w) |
| | FDC Red | 0.01 | 0.01 |
| | 50% ethanol | 80.00 | 80.00 |
| LL[3] | Hydroxypropyl Cellulose SSL | | 7.5 (93.75% w/w) |
| | Glycerin | | 0.16 (2.00% w/w) |
| | Talc | NA | 0.32 (4.00% w/w) |
| | FD&C Yellow | | 0.02 (0.25% w/w) |
| | Water | | 20.00 |

[1]UL refers to Upper Layer.
[2]ML refers to Middle Layer.
[3]LL refers to Lower Layer.
Note:
The solvents used in the manufacturing process were removed during the process of drying.

Manufacturing Process:

Preparation of upper layer: Dissolve menthol and then melatonin in 50% ethanol, then add sucralose, SLS, and color one after another and stir until a clear solution forms; then add HPC and stir until a clear viscous solution forms, and finally add talc and stir until uniform suspension forms.

Preparation of middle layer: Dissolve menthol and then active ingredients in 50% ethanol, then add sucralose, SLS, BHT, and color one after another and stir until a clear solution forms; then add HPMC and stir until a clear viscous solution forms, and finally add talc and stir until uniform suspension forms.

Preparation of lower layer: Dissolve HPC in water, then add color and stir until a clear solution forms, and finally add glycerin and talc and stir until uniform suspension forms.

First, coat the lower layer on a substrate. Then coat the middle layer on top of the dried lower layer, and finally coat the upper layer on the dried middle layer.

Remove the film from the substrate to form the oral transmucosal film.

Example 6-1 has two layers, and Example 6-2 has coating on all three layers.

The film prepared using the above formulas has a smooth and uniform appearance.

TABLE 7

| Stability Data of Example 6-1 in Accelerated Condition (40° C./75%RH) | | | |
|---|---|---|---|
| Parameters | Description | GABA Assay (%) | Vitamin B5 Assay (%) |
| Initial | Smooth and uniform film, upper layer is white, lower layer is yellow in color | 100.00 | 100.23 |
| 15 days | Smooth and uniform film, upper layer is white, lower layer is red in color | 98.83 | 99.63 |

TABLE 7-continued

| Stability Data of Example 6-1 in Accelerated Condition (40° C./75%RH) | | | |
|---|---|---|---|
| Parameters | Description | GABA Assay (%) | Vitamin B5 Assay (%) |
| 1 month | Smooth and uniform film, upper layer is white, lower layer is red in color with slightly oily surface | 95.53 | 97.21 |
| 3 months | Upper layer is white with non-uniform surface and lower layer is red in color with slightly oily surface | 91.73 | 95.37 |
| 6 months | Upper layer is white with non-uniform surface and lower layer is red in color with slightly oily surface | 88.67 | 93.41 |

TABLE 8

| Stability Data of Example 6-2 in Accelerated Condition (40° C./75%RH) | | | |
|---|---|---|---|
| Parameters | Description | GABA Assay (%) | Vitamin B5 Assay (%) |
| Initial | Smooth and uniform film, upper layer is white, lower layer is yellow in color | 100.03 | 99.76 |
| 15 days | Smooth and uniform film, upper layer is white, lower layer is yellow in color | 99.83 | 98.83 |
| 1 month | Smooth and uniform film, upper layer is white, lower layer is yellow in color | 99.26 | 97.21 |
| 3 months | Upper layer is white with non-uniform surface and lower layer is yellow in color | 98.63 | 95.69 |
| 6 months | Upper layer is white with non-uniform surface and lower layer is yellow in color | 95.23 | 93.91 |

The stability of the bilayer film of Example 6-1 is not so good. The lower layer showed some oily surface because of exposure of GABA, and the upper layer was non-uniform because of form conversion of melatonin. In Example 6-2, the stability results of GABA improved significantly but were not up to expectations, and the stability of vitamin B5 was not good. This could be due to the interaction between the drugs. Also, vitamin B5 is stable at neutral pH, and the instability could be because of pH of the microenvironment. In a further trial, the films were made by incorporating the active ingredients in different layers of tri-layer film. The suspension of the vitamin B5 layer was adjusted to neutral pH and polymer stabilizer was added to the upper layer.

Example 7: Formulation of Tri-Layer Film

In this experiment, drugs are incorporated in different layers and evaluated. Example 7-1 has vitamin B6 in the middle layer and vitamin B5 in the lower layer. Example 7-2 has vitamin B5 in the middle layer and vitamin B6 in the lower layer.

| Formulation: | | | |
|---|---|---|---|
| | Example | 7-1 | 7-2 |
| UL[1] | Melatonin | 3.00 (30.00% w/w) | 3.00 (30.00% w/w) |
| | Hydroxypropyl Cellulose SSL | 5.1 (5.1.00% w/w) | 5.1 (5.1.00% w/w) |
| | PVP | 1.00 (10.00% w/w) | 1.00 (10.00% w/w) |
| | Talc | 0.5 (5.00% w/w) | 0.5 (5.00% w/w) |
| | Sucralose | 0.1 (1.00% w/w) | 0.1 (1.00% w/w) |
| | menthol | 0.1 (1.00% w/w) | 0.1 (1.00% w/w) |
| | SLS | 0.1 (1.00% w/w) | 0.1 (1.00% w/w) |
| | FDC Red | 0.1 (1.00% w/w) | 0.1 (1.00% w/w) |
| | 50% ethanol | 50.00 | 50.00 |
| ML[2] | GABA (gamma-aminobutyric acid) | 3.00 (30.00% w/w) | 3.00 (25.00% w/w) |
| | Vitamin B5 | — | 2.00 (16.67% w/w) |
| | Vitamin B6 | 1.00 (10.00% w/w) | — |
| | HPMC 615 | 5.35 (53.50% w/w) | 6.22 (51.83% w/w) |
| | BHT | 0.30 (3.00% w/w) | 0.36 (3.00% w/w) |
| | Sucralose | 0.10 (1.00% w/w) | 0.12 (1.00% w/w) |
| | menthol | 0.10 (1.00% w/w) | 0.12 (1.00% w/w) |
| | SLS | 0.10 (1.00% w/w) | 0.12 (1.00% w/w) |
| | Titanium dioxide | 0.05 (0.5% w/w) | 0.06 (0.50% w/w) |
| | 50% ethanol | 65.00 | 70.00 |
| LL[3] | Vitamin B6 | — | 1.00 (12.5% w/w) |
| | Vitamin B5 | 2.00 (20.00% w/w) | — |
| | Hydroxypropyl Cellulose SSL | — | 6.66 (83.25% w/w) |
| | HPMC 615 | 7.38 (73.80% w/w) | — |

-continued

| Formulation: | | |
|---|---|---|
| Example | 7-1 | 7-2 |
| PVP | — | — |
| Talc | 0.4 (4.00% w/w) | 0.32 (4.00% w/w) |
| FD&C Yellow | 0.02 (0.20% w/w) | 0.02 (0.25% w/w) |
| Glycerin | 0.2 (2.00% w/w) | 0.16 (2.00% w/w) |
| Water | — | 20.00 |
| 50% ethanol | 70.00 | — |

[1]UL refers to Upper Layer.
[2]ML refers to Middle Layer.
[3]LL refers to Lower Layer.
Note:
(1) The solvents used in the manufacturing process were removed during the process of drying.
(2) The suspension of the lower layer of Example 6-1 adjusted to neutral pH of 7.

TABLE 9A

Stability Data of Examples 7-1 and 7-2 in Accelerated Condition (40° C./75%RH)

| Example Parameters | Description | GABA 7-1 | GABA 7-2 | Vitamin B5 7-1 | Vitamin B5 7-2 |
|---|---|---|---|---|---|
| | | Assay (%) | | | |
| Initial | Smooth and uniform film, upper layer is red, lower layer is yellow in color | 100.01 | 99.83 | 100.11 | 99.98 |
| 15 days | Smooth and uniform film, upper layer is red, lower layer is yellow in color | 99.56 | 100.06 | 99.93 | 98.72 |
| 1 month | Smooth and uniform film, upper layer is red, lower layer is yellow in color | 99.89 | 99.50 | 99.27 | 98.28 |
| 3 months | Smooth and uniform film, upper layer is red, lower layer is yellow in color | 98.83 | 98.89 | 98.69 | 97.67 |
| 6 months | Smooth and uniform film, upper layer is red, lower layer is yellow in color | 98.23 | 97.94 | 98.53 | 96.89 |

TABLE 9B

Stability Data of Examples 7-1 and 7-2 at Long-Term Condition (25° C./60%RH)

| Example Parameters | Description | GABA 7-1 | GABA 7-2 | Vitamin B5 7-1 | Vitamin B5 7-2 |
|---|---|---|---|---|---|
| | | Assay (%) | | | |
| Initial | Smooth and uniform film, upper layer is red, lower layer is yellow in color | 100.01 | 99.83 | 100.11 | 99.98 |
| 6 months | Smooth and uniform film, upper layer is red, lower layer is yellow in color | 99.87 | 98.94 | 100.00 | 97.83 |
| 12 months | Smooth and uniform film, upper layer is red, lower layer is yellow in color | 99.11 | 95.73 | 98.92 | 94.30 |

The stability results of Example 7-1 are better than Example 7-2. Degradation of both GABA and vitamin B5 was controlled. However, at the end of 12 months (see Table 9B), vitamin B5 in Example 7-2 was decreased to 94.30%, and there was a slight change in the appearance of the film in the lower layer and in the middle layer. This change was more pronounced in the middle layer, which indicates form conversion of GABA from amorphous to crystalline.

In view of the results, the inventors have decided to add a polymer to stabilize amorphous form in all the layers to avoid form conversion.

Example 8: Tri-Layer with Amorphous Form Stabilizer

To retain the amorphous form of all active ingredients, PVP polymer was used as an amorphous form stabilizer in all three layers.

| Formulation: | | |
|---|---|---|
| | Example | 8 |
| UL[1] | Melatonin | 3.00 (30.00% w/w) |
| | Hydroxypropyl Cellulose SSL | 5.1 (51.00% w/w) |
| | PVP | 1.00 (10.00% w/w) |
| | Talc | 0.5 (5.00% w/w) |
| | Sucralose | 0.1 (1.00% w/w) |
| | menthol | 0.1 (1.00% w/w) |
| | SLS | 0.1 (1.00% w/w) |
| | FDC Red | 0.1 (1.00% w/w) |
| | 50% ethanol | 50.00 |
| ML[2] | GABA (gamma-aminobutyric acid) | 3.00 (30.00% w/w) |
| | Vitamin B6 | 1.00 (10.00% w/w) |
| | HPMC 615 | 4.35 (43.50% w/w) |
| | PVP | 1.00 (10.00% w/w) |

-continued

| | Formulation: | |
|---|---|---|
| | Example | 8 |
| | BHT | 0.30 (3.00% w/w) |
| | Sucralose | 0.10 (1.00% w/w) |
| | menthol | 0.10 (1.00% w/w) |
| | SLS | 0.10 (1.00% w/w) |
| | Titanium dioxide | 0.05 (0.5% w/w) |
| | 50% ethanol | 65.00 |
| LL[3] | Vitamin B5 | 2.00 (20.00% w/w) |
| | HPMC 615 | 6.38 (63.80% w/w) |
| | PVP | 1.00 (10.00% w/w) |
| | Talc | 0.4 (4.00% w/w) |
| | FD&C Yellow | 0.02 (0.20% w/w) |
| | Glycerin | 0.2 (2.00% w/w) |
| | 50% ethanol | 70.00 |

[1]UL refers to Upper Layer.
[2]ML refers to Middle Layer.
[3]LL refers to Lower Layer.

Note: The solvents used in the manufacturing process were removed during the process of drying.

Sublingual films prepared according to Example 8 had good film property and a smooth appearance. They were easy to remove from the substrate, they were uniform in color, and the blend uniformity was satisfactory. In a dissolution test, the drug release was fast, completing in 30 minutes.

TABLE 10

Dissolution Test Result of Example 8

| | Media | pH 6.8 phosphate buffer, Volume 500 ml, USP II paddle method, rotation speed 50 rpm | | | | |
|---|---|---|---|---|---|---|
| | Time (min) | 5 | 10 | 15 | 20 | 30 |
| Melatonin | Dissolved | 38 | 55 | 86 | 95 | 99 |
| GABA | (%) | 50 | 72 | 87 | 99 | 99 |
| Vitamin B5 | | 39 | 56 | 80 | 93 | 100 |
| Vitamin B6 | | 59 | 73 | 88 | 97 | 100 |

In similar experiments, other film-forming agents such as polyethylene glycol and polyvinyl alcohol graft copolymer (PEG-PVA), polyvinyl alcohol (PVA), polyvinyl pyrrolidone (PVP), hydroxyethyl cellulose, pullulan, sodium carboxymethyl cellulose (CMC-Na), xanthan gum, tragacanth gum, guar gum, polyacrylic acid, high amylose starch, hydroxypropylated high amylose starch, collagen, gelatin pectin, copovidone, and povidone were tested in the upper, middle, and lower layers. The quantity in the upper layer was within the range of 40-80% w/w. The quantity in the middle layer was within the range of 38-53% w/w. The quantity in the lower layer was within the range of 40-72% w/w. The results show that the film integrity was good and dissolution of the film was good.

In similar experiments, other solubilizers such as hydroxypropyl-β-cyclodextrins, polysorbate, and poloxamers were tested in the upper and middle layers. The quantity in the upper layer was within the range of 0.5-5% w/w and in the middle layer was within the range of 0.5-5% w/w. The results show that the film integrity was good and the dissolution of the film was good.

In similar experiments, other amorphous form stabilizers such as sodium alginate, polyvinyl pyrrolidone, chitosan, and polyethylene glycol were used in the upper, middle, and lower layers and then tested. The quantity in the upper layer was within the range of 8-20% w/w. The quantity in the middle layer was within the range of 8-20% w/w. The quantity in the lower layer was within the range of 8-20% w/w. The results show that the amorphous forms of all active ingredients were intact, and no form conversion was observed.

In similar experiments, other antioxidants such as ascorbyl palmitate and gallic acid monohydrate were used in the middle layer and tested. The results show that no degradation was found.

In similar experiments, other hydrophobic stabilizers such as stearic acid, magnesium stearate, calcium stearate, and sodium stearyl fumarate were tested in both the upper and lower layers. The results show that the film was intact and no degradation was found.

Example 9: Drug and Excipient Concentration Range Evaluation

In these experiments, the concentrations of active ingredients, film-forming materials, and other excipients were evaluated. The formulation details are given below.

| | Formulation: | | | |
|---|---|---|---|---|
| | Example | 9-1 | 9-2 | 9-3 |
| UL[1] | Melatonin | 0.55 (5.00% w/w) | 10.00 (50.00% w/w) | 0.6 (5.00% w/w) |
| | Hydroxypropyl Cellulose SSL | 8.80 (80.80% w/w) | 7.9 (39.50% w/w) | 6.42 (53.50% w/w) |
| | PVP | 0.88 (8.00% w/w) | 1.6 (8.00% w/w) | 2.40 (20.00% w/w) |
| | Talc | 0.55 (5.00% w/w) | 0.10 (0.50% w/w) | 1.20 (10.00% w/w) |
| | Sucralose | 0.055 (0.50% w/w) | 0.10 (0.50% w/w) | 0.12 (1.00% w/w) |
| | menthol | 0.055 (0.50% w/w) | 0.10 (0.50% w/w) | 0.6 (5.00% w/w) |
| | SLS | 0.055 (0.50% w/w) | 0.10 (0.50% w/w) | 0.6 (5.00% w/w) |
| | FDC Red | 0.055 (0.05% w/w) | 0.10 (0.50% w/w) | 0.06 (0.50% w/w) |
| | 40% ethanol | 50.00 | 55.00 | — |
| | 80% ethanol | — | — | 50.00 |
| ML[2] | GABA (gamma-aminobutyric acid) | 7.00 (38.89% w/w) | 3.00 (30.00% w/w) | 3.00 (16.70% w/w) |
| | Vitamin B6 | 0.50 (2.78% w/w) | 2.00 (20.00% w/w) | 0.5 (2.78% w/w) |
| | HPMC 615 | 6.81 (37.83% w/w) | 3.93 (39.30% w/w) | 9.60 (53.32% w/w) |
| | PVP | 1.44 (8.00% w/w) | 0.8 (8.00% w/w) | 3.60 (20.00% w/w) |
| | BHT | 1.08 (6.00% w/w) | 0.15 (1.5% w/w) | 0.27 (1.50% w/w) |
| | Sucralose | 0.09 (0.50% w/w) | 0.01 (0.10% w/w) | 0.02 (0.10% w/w) |
| | menthol | 0.90 (5.00% w/w) | 0.05 (0.50% w/w) | 0.09 (0.50% w/w) |
| | SLS | 0.09 (0.50% w/w) | 0.05 (0.50% w/w) | 0.9 (5.00% w/w) |

-continued

| | Formulation: | | | |
|---|---|---|---|---|
| | Example | 9-1 | 9-2 | 9-3 |
| | Titanium dioxide | 0.09 (0.50% w/w) | 0.01 (0.1% w/w) | 0.02 (0.1% w/w) |
| | 50% ethanol | 70.00 | 65.00 | — |
| | 80% ethanol | — | — | 77.00 |
| LL[3] | Vitamin B5 | 6.00 (50.00% w/w) | 2.00 (20.00% w/w) | 2.00 (16.65% w/w) |
| | HPMC 615 | 4.70 (39.40% w/w) | 4.68 (46.80% w/w) | 8.73 (72.75% w/w) |
| | PVP | 1.00 (8.00% w/w) | 2.00 (20.00% w/w) | 0.96 (8.00% w/w) |
| | Talc | 0.2 (2.00% w/w) | 0.8 (8.00% w/w) | 0.24 (2.00% w/w) |
| | FD&C Yellow | 0.01 (0.10% w/w) | 0.02 (0.20% w/w) | 0.01 (0.10% w/w) |
| | Glycerin | 0.1 (0.50% w/w) | 0.5 (5.00% w/w) | 0.06 (0.50% w/w) |
| | 50% ethanol | 70.00 | 70.00 | 73.00 |

[1]UL refers to Upper Layer.
[2]ML refers to Middle Layer.
[3]LL refers to Lower Layer.
Note:
The solvents used in the manufacturing process were removed during the process of drying.

The sublingual films prepared according to the above formulas all had acceptable film properties. The dissolution experiments showed fast and acceptable release data. The stability data showed acceptable results.

Example 10: Clinical Study

In this example, a randomized double-blind, placebo-controlled parallel study was performed on 26 middle-aged patients (40-55 years) with primary insomnia. The patients were randomized in 1:1 ratio to receive sublingual film of Example 8 (n=13) or placebo (n=13) for 4 weeks. All patients provided written informed consent prior to study participation. During the screening, medical histories, psychiatric status and medication, symptoms of primary insomnia, and difficulty in initiating and/or maintaining sleep and/or poor quality of sleep 1 month or more with significant daytime distress were assessed. Additionally, a physical examination was conducted by a qualified clinician. Exclusion criteria included use of hypnotics or any psychoactive treatment within the previous 1 month and use of drugs such as neuroleptics, antidepressants, and anticholinergic agents that could interfere with sleep patterns. Sleep parameters tested by overnight polysomnography (PSG), subjective sleep performance, and daytime somnolence obtained from the Pittsburgh Sleep Quality Index (PSQI), Insomnia Severity Index (ISI), and Epworth Sleepiness Scale (ESS) were obtained at baseline and after treatment. Treatment was administered daily one hour before bedtime.

The beginning of PSG recordings was set at 22:30 and termination of PSG recordings was set at 7:00. Scoring was performed automatically using computer software and scores were subsequently checked manually by a skilled technician.

The PSQI has been recommended as an essential measure for global insomnia symptoms. The PSQI is a self-rating scale that assesses 7 domains of sleep: sleep latency, sleep duration, sleep efficiency, sleep quality, sleep disturbances, medication, and daytime dysfunction. A summation score yields a global score, ranging from 0 to 21. Insomnia was defined as a global score of >5 (sensitivity of 90% and specificity of 87% in the general population).

The ISI is a useful tool in measuring outcome after insomnia treatment. This questionnaire has seven items that evaluate insomnia symptoms (initial, middle, late), the degree of satisfaction with sleep, interference with daytime functioning, noticeability of impairment, and concern caused by the sleep problem. The ISI uses a Likert scale of 5 points (0=none; 4=extremely severe), yielding a total score between 0 and 28. A score of 14 provides the best cutoff for optimizing sensitivity and specificity.

The ESS is the preferred self-report measure of sleepiness, providing a subjective approach to evaluate daytime sleepiness in the form of a self-reported 8-item questionnaire evaluating sleep propensity in eight daily situations. ESS score is calculated by totaling the sub-scores with a response format of 4-point Likert (0=no drowsiness, 1=slight drowsiness, 2=moderate drowsiness, and 3=severe drowsiness). In addition, the total score ranges from 0 to 24. The higher the score, the higher the level of severity for daytime sleepiness.

The results presented in Tables 11 and 12 show that treatment using sublingual films of Example 8 leads to an overall improvement in insomnia. The films of Example 8 significantly decreased the sleep latency from time 56±45 to 40±22 min (baseline to follow-up); similarly, total sleep time improved from 339±78 to 390±59 min, sleep efficiency improved from 75±18% to 87±13%, and awakening during sleep was reduced from 45±41 to 30±22. The subjective sleep parameters, PSQI total score, ISI, and ESS results showed significant improvement in the self-rating scale, with the rating showing improvement in sleep quality, degree of satisfaction with sleep, and level of concern caused by the sleep problem. No serious adverse events were reported.

TABLE 11

Effect of Example 8 Treatment on Objective Sleep Parameters

| | Placebo group | | Example 8 group | |
|---|---|---|---|---|
| | Baseline | Follow-up | Baseline | Follow-up |
| Sleep latency (min) | 60 ± 40 | 54 ± 36 | 56 ± 45 | 40 ± 22 |
| Total sleep time TST (min) | 345 ± 73 | 340 ± 71 | 339 ± 78 | 390 ± 59 |
| Sleep efficiency (%) | 74 ± 15 | 75 ± 17 | 75 ± 18 | 87 ± 13 |
| Awakening during sleep (min) | 50 ± 47 | 45 ± 46 | 45 ± 41 | 30 ± 22 |
| Early wake (min) | 36 ± 31 | 41 ± 32 | 38 ± 41 | 45 ± 44 |

Sleep efficiency was calculated as 100*TST/time in bed.
Sleep latency was calculated as the time elapsed between light off and sleep onset.
Awakening during sleep was defined as total time duration of awakenings.
Early wake time was defined as light-on time of PSG recording minus wake-up time.

TABLE 12

Effect of Example 8 Treatment on Subjective Sleep Parameters

| | Placebo group | | Example 8 group | |
|---|---|---|---|---|
| | Baseline | Follow-up | Baseline | Follow-up |
| PSQI total score | 11.23 ± 4.24 | 8.11 ± 3.46 | 10.83 ± 4.11 | 6.11 ± 3.12 |
| ISI | 14.56 ± 5.79 | 11.23 ± 4.37 | 12.63 ± 5.00 | 8.56 ± 3.98 |
| ESS | 9.11 ± 5.23 | 8.23 ± 4.58 | 8.68 ± 5.71 | 7.86 ± 4.13 |

The invention, and the manner and process of making and using it, are now described in full, clear, concise, and exact terms so as to enable any person skilled in the art to which it pertains to make and use the same. It is to be understood that the foregoing describes preferred embodiments of the present invention, and that modifications can be made therein without departing from the scope of the present invention as set forth in the claims. To particularly point out and distinctly claim the subject matter regarded as the invention, the following claims conclude this specification.

What is claimed is:

1. An oral sublingual tri-layer film, comprising:

(a) an upper layer comprising 5-50% by weight of melatonin, 40-80% by weight of a first film-forming material, 0.5-5% by weight of a first solubilizer, 8-20% by weight of a first amorphous form stabilizer, and 0.5-10% by weight of a first hydrophobic stabilizer, wherein the % by weight in (a) is based on the total weight of the upper layer;

(b) a middle layer comprising 16.70-38.89% by weight of gamma-aminobutyric acid (GABA), 3-20% by weight of vitamin B6, 38-53% by weight of a second film-forming material, 1.5-6% by weight of an antioxidant, 0.5-5% by weight of a second solubilizer, and 8-20% by weight of a second amorphous form stabilizer, wherein the % by weight in (b) is based on the total weight of the middle layer; and (c) a lower layer comprising 16.65-50% by weight of vitamin B5, 40-72% by weight of a third film-forming material, 5-25% by weight of a third amorphous form stabilizer, and 2-8% by weight of a second hydrophobic stabilizer, wherein the % by weight in (c) is based on the total weight of the lower layer;

wherein the first, the second, and the third film-forming materials are independently selected from the group consisting of hypromellose (HPMC), hydroxypropyl cellulose (HPC), polyethylene glycol and polyvinyl alcohol graft copolymer (PEG-PVA), polyvinyl alcohol (PVA), polyvinyl pyrrolidone (PVP), hydroxyethyl cellulose, pullulan, sodium carboxymethyl cellulose (CMC-Na), xanthan gum, tragacanth gum, guar gum, polyacrylic acid, high amylose starch, hydroxypropylated high amylose starch, collagen, gelatin pectin, copovidone, povidone, and any combination thereof;

wherein the first and the second solubilizers are independently selected from the group consisting of: hydroxypropyl-β-cyclodextrins, sodium lauryl sulfate, polysorbate, poloxamers, and any combination thereof;

wherein the first and the second hydrophobic stabilizers are independently selected from the group consisting of talc, stearic acid, magnesium stearate, calcium stearate, sodium stearyl fumarate, and any combination thereof;

wherein the antioxidant is selected from the group consisting of: butylated hydroxytoluene, butylated hydroxyanisole, citric acid, ascorbyl palmitate, gallic acid monohydrate, and any combination thereof; and wherein the first, the second, and the third amorphous form stabilizers are independently selected from the group consisting of sodium alginate, polyvinyl pyrrolidone, chitosan, polyethylene glycol, and any combination thereof.

2. The film according to claim 1, wherein the melatonin is in amorphous form.

3. The film according to claim 1, wherein the GABA and the vitamin B6 are in amorphous forms.

4. The film according to claim 1, wherein the vitamin B5 is in amorphous form.

5. The film according to claim 1, wherein the is first, the second, and the third film-forming materials are independently selected from the group consisting of HPMC, HPC, PEG-PVA, PVA, PVP, hydroxyethyl cellulose, pullulan, and any combination thereof.

6. The film according claim 1, having a size between 1 cm×1 cm and 3 cm×3 cm.

7. The film according to claim 1, wherein the antioxidant is butylated hydroxytoluene, ascorbyl palmitate, or gallic acid monohydrate.

8. The film according to claim 1, comprising 0.55-10 mg of melatonin, 3-7 mg of GABA, 2-6 mg of vitamin B5, and 0.5-2 mg of vitamin B6.

9. The film according to claim 1, wherein each of the upper layer, the middle layer, and the lower layer independently comprises 0.5-5% by weight of a flavoring agent.

10. The film according to claim 1, wherein the lower layer further comprises a plasticizer selected from the group consisting of PEG 400, triethyl citrate, glycerin, and a combination thereof.

11. The film according to claim 1, further comprising one or more sweeteners in one or more layers of the upper layer, the middle layer, or the lower layer.

12. The film according to claim 11, comprising 0.5-5% w/w of the one or more sweeteners in each of the upper layer, the middle layer, and the lower layer, wherein the one or more sweeteners are selected from the group consisting of sucrose, glucose, sodium saccharin, fructose, xylitol, stevia, aspartame, sucralose, neotame, acesulfame potassium, and any combination thereof.

13. A process for preparing the oral sublingual tri-layer film according to claim 1, comprising the steps of:

(a) mixing melatonin, the first solubilizer, the first film-forming material, the first amorphous form stabilizer, and the first hydrophobic stabilizer in a first solvent to form a uniform suspension of the upper layer;

(b) mixing GABA, vitamin B6, the second solubilizer, the second film-forming agent, the second amorphous form stabilizer, and the antioxidant in a second solvent to form a uniform suspension of the middle layer;

(c) mixing vitamin B5, the third film-forming material, the third amorphous form stabilizer, and a second hydrophobic stabilizer in a third solvent to form a uniform suspension of the lower layer;

(d) coating the lower layer suspension on a substrate, and drying the lower layer suspension;

(e) coating the middle layer suspension on the dried lower layer suspension and drying the middle layer suspension;

(f) coating the upper layer suspension on the dried middle layer suspension; and (g) removing the dried three-layer suspension from the substrate to form the oral sublingual tri-layer film.

14. The process of claim 13, wherein the first solvent, the second solvent, and the third solvent are 40-80% ethanol.

15. A method for treating insomnia in a subject, comprising the steps of:

identifying a subject in need thereof; and placing the oral sublingual tri-layer film of claim 1 in sublingual mucosa of the subject.

* * * * *